United States Patent

Stockhausen et al.

[11] Patent Number: 5,837,789
[45] Date of Patent: Nov. 17, 1998

[54] FLUID-ABSORBING POLYMERS, PROCESSES USED IN THEIR PRODUCTION AND THEIR APPLICATION

[75] Inventors: Dolf Stockhausen, Krefeld; Hans-Georg Hartan, Kevelaer; Helmut Brehm, Krefeld; Gerd Jonas, Kempen, all of Germany; Bernfried Messner, Greensboro, N.C.; Klaus Pflueger, Krefeld, Germany

[73] Assignee: Stockhausen GmbH & Co. KG, Krefeld, Germany

[21] Appl. No.: 752,889

[22] Filed: Nov. 20, 1996

[30] Foreign Application Priority Data

Nov. 21, 1995 [DE] Germany ............... 195 43 369.6
Nov. 11, 1996 [DE] Germany ............... 196 46 484.6

[51] Int. Cl.$^6$ .................. C08F 220/28; C08F 220/18; C08F 220/56; C08F 226/02
[52] U.S. Cl. ............... 526/320; 526/329.6; 526/310; 526/306; 526/317.1; 526/303.1; 526/307.1; 526/264
[58] Field of Search .................... 526/320, 329.6, 526/310, 306, 317.1, 303.1, 307.1, 264

[56] References Cited

U.S. PATENT DOCUMENTS

| | | |
|---|---|---|
| 5,086,133 | 2/1992 | Itoh et al. . |
| 5,408,019 | 4/1995 | Mertens et al. . |
| 5,506,324 | 4/1996 | Gartner et al. . |
| 5,532,323 | 7/1996 | Yano et al. .................. 525/384 |
| 5,548,047 | 8/1996 | Ito et al. . |

FOREIGN PATENT DOCUMENTS 2179775  6/1995  Canada .

*Primary Examiner*—Jeffrey T. Smith
*Assistant Examiner*—Wu C. Cheng
*Attorney, Agent, or Firm*—Foley & Lardner

[57] ABSTRACT

The present invention relates to superabsorbent cross-linked polymers for watery liquids, which are built-up of partially neutralized monomers having monoethylenlcally unsaturated acid groups, optionally further monomers copolymerizable therewith, as well as polymers optionally suitable as graft basis, and which can be manufactured by using a cross-linker/monomer combination of $CH_2=CHR^6-CO-(OCHR^3-CHR^3)_zO-CH_2-CHR^6=CH_2$ $CH_2=CHR^6-R^5-(OCHR^3-CHR^3)_vOR^4$ $R^1-[O(CHR^3-CHR^3O)_u-CO-R^2]_x$, and/or di- or triallylamine and/or bisacrylamide with $R^1$: multivalent C2–10-alkyl,
$R^2$: linear or branched C2–10-alkenyl,
$R^3$: H, $CH_3$, $C_2H_5$,
$R^4$: H, linear or branched C1–10-alkyl,
$R^6$: CO, $CH_2$
$R^8$: H, $CH_3$
x: 2–6
u: 0–15
V: 1–45
z: 3–20

As compared with the state of the art, the polymers according to the present invention have an improved combination of the properties retention, liquid absorption under pressure at 63 g/cm$^2$ and soluble contents, moreover, they have an Increased permeability of the gel layer for watery liquids, a high suction rate, and a high swelling pressure. The polymers are used as absorbents for water and watery liquids in constructions for the absorption of body fluids, In electricity or light-conducting cables, and in plant raising.

23 Claims, No Drawings

FLUID-ABSORBING POLYMERS, PROCESSES USED IN THEIR PRODUCTION AND THEIR APPLICATION

The invention concerns superabsorbing polymers for watery liquids, processes used in their production and their application. The polymers, based on monomers containing carboxylate groups and obtained by a special combination of cross-linking agents and other comonomers, show a combination of properties never attained before with regard to absorption rate, high retention at high absorption under pressure, low soluble content and good permeability of the gel layer for watery liquids under pressure load and stable surface cross-linkage.

Superabsorbent polymers are water-insoluble cross-linked polymers which are capable through swelling and with the formation of hydrogels of absorbing large quantities of watery liquids and body fluids such as urine and blood and of retaining the absorbed amount of fluid under a certain pressure. Because of these typical absorption properties the polymers are mostly used for integrating into sanitary articles such as diapers and ladies' napkins.

Commercially available superabsorbent polymers are mainly cross-linked polyacrylic acids or cross-linked starch/acrylic acid graft copolymers in which the carboxyl groups are partly neutralized with sodium or potassium ions.

The production of superabsorbent polymers is mainly carried out by polymerisation of watery solutions of mixtures of partly-neutralized acrylic acid and cross-linking agent to a polymer gel which is mechanically broken up into small pieces, dried and then ground to a certain particle size. Alternatively, polymer powders can also be obtained by inverse suspension polymerisation in which the watery monomer phase in an oil phase, consisting, for example, of cyclohexane, is suspended with auxiliary agents and then poymerised. By azeotropic distillation the water contained in the polymer droplets is removed and the polymer particles then isolated by filtering off from the oil phase.

In the course of the continued technical development of superabsorbing polymers the demands made on these products has changed markedly over the years. While during the development of the superabsorbers only the very high swelling capacity on contact with liquid was of prime importance at first, it later turned out that not only the amount of absorbed liquid was important, but also the firmness of the swollen gel. Retention on the one hand and gel firmness on the other are, however, opposing properties, as is known from U.S. Pat. No. 3,247,171 and Reissue Pat. No. 32,649. This means that polymers with a particularly high retention show only a low level of firmness of the swollen gel, with the result that the gel can be deformed under an applied pressure (e.g. body pressure) and further liquid absorption prevented. Therefore a balance between retention and gel strength has to be striven for so that in use fluid absorption can also take place against an applied pressure. This specific absorption characteristic is termed absorption under pressure in EP 339 461.

The method of measuring the fluid take-up under pressure (AUL) is carried out under various loads. In the course of the increased demands on superabsorbers it has turned out that the original test load of 21 $g/cm^2$ (0.3 psi) no longer measures the desired quality standard as required for incontinence products or for diaper designs with low fluff content and high amounts of superabsorber. Accordingly pressure loads are measured today at 42 $g/cm^2$ (0.6 psi) and preferably at 63 g/cm2 (0.9 psi).

The increasing tendency to design sanitary articles ever smaller and thinner can only be fulfilled by reducing the voluminous fluff component In the diaper and at the same time increasing the proportion of superabsorber. Here the superabsorber has to take over additional tasks with regard to fluid absorption and transport which were previously carried out by the fluff.

The characteristics of the superabsorbers can be improved by the process of subsequent surface cross-linkage, in particular their fluid absorption under pressure, as the well-known phenomenon of "gel blocking" is suppressed, in which swollen polymer particles stick together and prevent any further absorption and distribution of fluid in the diaper. During the subsequent cross-linking process the carboxyl groups of the polymer molecules are cross-linked on the surface of the super-absorber particles with crosslinking agents at a raised temperature. Among other agents, multivalent metal salts, glycidyl compounds, polyols, polyepoxides, polyamines, alkylene carbonates and polyethylene glycols are used. Subsequent cross-linking can be carried out several times. It is clear from the patent literature that the increased fluid absorption under pressure is associated with a marked reduction in retention. There is therefore a requirement for superabsorber starting products which show a less marked drop in the retention values in subsequent cross-linking. Moreover, it has not been possible so far to fix the surface cross-linkage permanently to the polymer backbone. For this reason, most of the effects obtained by surface cross-linking are destroyed again by mechanical actions exerted on the absorber.

For the processing of the superabsorbers various screening fractions are used, depending on the application, e.g. for diapers between 100 and 800$\mu$, for cable insulation under 200$\mu$. This means that in the case of the application in cables the fine constituents of the superabsorbers are of advantage because of their tendency to gel blocking, as this blocks off the water penetrating the cable. In the diaper this effect is not desired as it impedes the absorption and distribution of fluid, and so larger screening fractions are selected.

Besides a high degree of retention and fluid absorption under pressure superabsorbers have to contain low soluble constituents which arise due to Incomplete cross-linking during the polymerization reaction and which are not fully retained in the body of the polymer when applied. This finally leads to a reduction in the capacity of the superabsorber to absorb and distribute fluid in the diaper. The limiting values quoted for low soluble constituents, for example. in the Reissue Pat. No. 32,649 are 7.5% after 1 hour and 17% after 16 hours. Compared to the product properties desired by present-day producers of hygiene articles, these limiting values for the soluble constituents are far too high.

The optimization of application properties of the superabsorbing polymers was carried out in the past mainly by varying the type and amount of cross-linking agent, by the pH value during polymerization and by after-treatment of the polymer particles in the form of a coating or subsequent surface cross-linking. So far, however, it has not been possible to make available any superabsorber combining the properties of high retention, high AUL (63 $g/cm^2$, 0.9 psi) and low soluble contents and at the same time high permeability in the gel layer for watery liquids under pressure load, high rate of absorption and lasting surface cross-linkage.

The basis of WO 94/09043 is the problem of developing new superabsorbing polymers with increased absorption capacity for watery liquids, even under pressure. It describes the solution to this problem as double cross-linked superabsorbers whose first stage of production is cross-linking during polymerization with methylene bisacrylamide, bis (acrylamido)acetic acid, allyl acrylate, allyl methacrylate, esters or amides with terminal vinyl and allyl functions or highly ethoxylated trimethylol propane triacrylate and as a second stage the coating of the resulting polymer particles on the surface with a cross-linking agent, followed by cross-linking. In this process, which is not new, the preferred surface cross-linking agents are polyhydroxy compounds which are applied together with water or water/solvent mixtures and caused to react at raised temperatures (175°–230° C.) after the moisture in the polymer gel of the first stage has been at least partly removed.

By the combination of one of the above-mentioned primary cross-linking agents with the secondary surface cross-linking agents unique product properties are said to be obtained with regard to retention and fluid absorption under pressure, making it possible for them to be used in hygiene articles in which the absorbing polymers have to take up considerable amounts of fluid and retain them even under pressure. When the results of the trials are examined it is noticeable that the polymers show a marked improvement in their properties simply by being stored at a high temperature without the addition of a subsequent cross-linking agent. Subsequent cross-linking produces a further increase in fluid absorption under pressure at 42 g/cm$^2$ (0.6 psi). These AUL values are then in a range between 10 and 26 gig, depending on the type, whereby the products with the highest AUL values only reach absorption values of 30 g/g. Absorption values of over 30 gig are, as example 3B (absorption 35 g/g and AUL 16.5 gig) shows, only possible at the expense of the AUL at 42 g/cm$^2$ (0.6 psi). This makes it clear that the products with the special cross-linking combination contained in WO 94109043 in no way meets the high demands made today on such cross-linked polymers, i.e. the peak values measured therein for 42 g/cm$^2$ (0.6 psi) are required today for a higher load at 63 g/cm$^2$ (0.9 psi), combined with absorption values of markedly greater than 30 gig.

WO 93/121237 describes superabsorbent polymers which are cross-linked with unsaturated esters of polyalkyl glycols and which, through a subsequent heating process, achieve an improvement in properties with regard to retention and liquid absorption under a low pressure of 21 g/cm$^2$ (0.3 psi) of up to 25 g/g. Ethoxylated trimethylol propane triacrylate is the preferred cross-linking agent, whereby the number of EO units per polyglycol chain can be between 2 and 7. According to this paper the use of non- or only slightly ethoxylated trimethylol propane triacrylate leads to considerably worse properties of the superabsorber which is cross-linked with it. Analagous to the polymers in WO 94/09043 the products described here also do not fulfil the demands placed today on absorption under a higher pressure at 63 g/cm$^2$ (0.9 psi). In diagram 13 on page 818 of WO 93/21237, which shows the process of fluid absorption under pressure for various pressure loads, the weakness of the polymers described there can be seen quite dearly, whose measured values of approximately 18 g/g in the interesting pressure load range of 63 g/cm$^2$ (0.9 psi) are totally unsatisfacory. This all the more so when the measured values were obtained on a very unusual screening fraction of 300–800$\mu$m which per se results in higher measured values than the screening fraction of 150–800$\mu$m usual in the field.

Reissue Pat. No. 32,649 deals with the production of non-grafted superabsorbent polymers with a high gel volume, high gel strength, measured via the shear modulus and low soluble contents. The gel volume should be at least 20 g/g and the maximum value of the soluble components, measured after 1 hour, should not exceed 7.5% and in the state of equilibrium after 16 hours be no more than 17%.

Preferably the polymers should be polymerized in a low watery starting concentration of 8 to 24 % by weight from acrylic acid which is not neutralized. cross-linkage preferably takes place with N,N'-methylene bisacrylamide, trimethylol propane triacrylate or triallylamine. This is followed by crushing, neutralization, grinding and drying.

The production process described in Reissue Pat. No. 32,649 contains important drawbacks in the method, On the one hand the low starting concentration and the subsequent heating of the polymer gel over several hours means that the space-time yield is low, and on the other hand the stop of subsequent neutralization of the solid polymer gel is technically very time-consuming and cannot be carried out to the same quality as neutralization in the preceding solution can be. Polymer gels neutralized subsequently are, as a rule, not neutralized consistently and often discolored due to the irregular distribution of alkali. As a consequence of the uneven neutralization strong fluctuations in the quality of the product can arise.

EP 690 077 describes superabsorbers having an improved breaking strength by using polyethylene glycols and derivatives, such as methoxypolyethylene glycol methacrylates used as additives or comonomers. The superabsorbers are distinguished by the fact that there are less particles in the range <5 $\mu$m in a grinding test when compared with a reference product. There are no statements with respect to the swelling properties of the superabsorbers after mechanical load. The described superabsorbers are neither produced with special pre-cross-linking agents nor with subsequent surface cross-linking agents. The indicated absorptions under a pressure of at least 17 g/g, preferably >20 g/g (AUL) merely relate to an extremely low load of about 20 g/cm$^2$ and—measured against the art—are not in an acceptable region. For quite a long time, prior art superabsorbers provide higher absorptions under a higher pressure (63 g/cm$^2$) of >20 g/g. On the other hand, using polyethylene glycols to dedust superabsorbers is known.

In WO 94/122940 superabsorbent polymers with a small dust component are described which arise due to a surface coating with polo or polyethylene glycol and which show liquid absorption under low pressure at 21 g/cm$^2$ (0.3 psi) of >20 g/g. The treatment of superabsorbers with such substances has already been described in WO 93/21237 (page 12, line 15). This version showing improved abrasion and reduced dust requires, however, an additional step in the manufacturing process.

At present there are no prior art documents concerning the manufacture of superabsorbers with the desired combination of properties of high permeability for watery liquids, stable surface cross-linkage, high retention, high absorption rate, pressure-resistant hydrogel and a low soluble component.

Low soluble components are also a precondition for superabsorbers which have to show a practical swelling pressure over a long time. If the amount of soluble contents is over 12% the superabsorber can no longer, after being subjected to pressure for 16 hours, in a diaper for example, store the amount of fluid required for application technological reasons.

The permeability in the layer (i.e., in x,y-direction) of the absorbent article comprising the superabsorber particularly gains in importance when constructions are used having an ever reducing fluff amount with a simultaneously increasing superabsorber amount. This additionally gains in importance if the liquid distribution has to take place under a pressure of 50 g/cm$^2$, for example. A suitable method to determine the permeability of a gel layer in x,y-direction under pressure is the method of determining the absorption under pressure through a size-reduced aperture in the bottom of a so-called AAP-cylinder unit. The AAP-cylinder unit is described in EP 640 330 on page 14 (Absorption against Pressure test).

Superabsorbent polymers which are to meet today's state of the art with respect to absorbent article construction, must support the liquid transport in x,y-direction, i.e., within the gel layer, such that highest possible absorption values are achieved in the mentioned measuring method. The measured values are then calculated against the respective absorption against pressure at the same load (20 g/cm$^2$ or 50 g/cm$^2$) and are expressed as percentage absorption. The demands placed on diapers comprising larger amounts of superabsorber require values in the range of >50%; for the surface-reduced AAP-value at least 15 g/g must be achieved.

The object of the present invention is to provide new polymers and a process for making them. These polymers were to be used as superabsorbers in diapers or other technical applications and were to have an improved combination of properties with regard to retention, fluid absorption under pressure at 63 g/cm$^2$ (0.9 psi) and soluble components, and which, due to their polymer composition, were to have an efficient and lasting surface cross-linkage and, due to their permeability, permit a good liquid distribution in swollen condition even under pressure (50 g/cm$^2$). Moreover, the superabsorbers should possess a high suction rate and a high swelling pressure.

Surprisingly it was found that cross-linked polymers absorbing watery liquids, built-up of partially neutralized monomers having monoethylenically unsaturated acid groups and optionally further monomers copolymerizable therewith as well as optional water-soluble polymers suitable as graft basis, that are produced using a cross-linker combination of

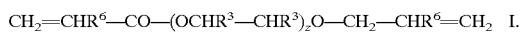
$$CH_2=CHR^6-CO-(OCHR^3-CHR^3)_zO-CH_2-CHR^6=CH_2 \quad \text{I.}$$

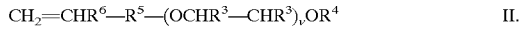
$$CH_2=CHR^6-R^5-(OCHR^3-CHR^3)_vOR^4 \quad \text{II.}$$

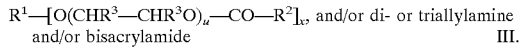
$$R^1-[O(CHR^3-CHR^3O)_u-CO-R^2]_x, \text{ and/or di- or triallylamine and/or bisacrylamide} \quad \text{III.}$$

with $R^1$: multivalent C2–10-alkyl
$R^2$: linear or branched C2–10-alkenyl
$R^3$: H, $CH_3$, $C_2H_5$,
$R^4$: H, linear or branched C1–10-alkyl,
$R^5$: CO, $CH_2$,
$R^6$: H, $CH_3$,
x: 2–6
u: 0–15
v: 1–45
z: 3–20 and are then subjected to surface cross-linkage have a retention of greater than 30 g/g and a liquid absorption under pressure at 63 g/cm$^2$ (AUL 0.9 psi) of greater than 20 g/g, and their soluble contents after 1 hour are less than 6.5% and after 16 hours less than 10%, and their permeability within the gel layer permits to use at least 50%-test (Absorption against Pressure with a suction surface reduced by x %) with at least 15 g/g, preferably at least 20 g/g AAP50-A$_x$. Due to the preferably at least 60% of absorption capacity under a load of 50 g/cm$^2$ in the AAP-A$_x$. polymer structure, which is achieved according to the present invention, an improved and lasting cross-linkage between the polymer and the surface cross-linking agent takes place. This is shown in the fact that the AUL (63 g/cm$^2$, after a loading test to determine the stability of the surface cross-linkage, still has values of greater than 18 g/g, and this suggests an extraordinarily stable surface cross-linkage and an extremely thorough reaction with the surface cross-linking agent.

The cross-linking agents thus invented according to formula I contain a (meth)allyl function and a (meth)acrylic acid ester function as well as a hydrophilic chain situated between these two functions consisting of at least three, but preferably five to twenty ethylene oxide units. The used of mixed ethylene oxide/propylene oxide chains, which can be produced as random or block copolymers, is possible. The solubility of the cross-linking agent in the monomer solution to be polymerized can be adjusted by the relationship of EO/PO units. The cross-linkers can be produced, for example, by esterification of alkoxylated allyl alcohol with (meth)acryllc acid. In the newly invented cross-linking agents there may be residues of starting components to be found due to the manufacturing process which do not, however, have a negative effect on the properties of the superabsorber. The cross-linking agents according to formula I or their mixtures are used in a ratio of 0–1.0% by weight or preferably 0.05–0.6% by weight, or even better 0.1–0.4% by weight with regard to the whole monomers.

The newly-invented monomers to be used with the cross-linkers according to formula II are preferably (meth)acrylic acid ester or (meth)allyl alcohol ether from polyalkylene glycols. A preferred type is the polyoxyalkylene glycol chain with a terminal alkyl residue. The C number in the alkyl residue is in the range 1–10, preferably in the range 1–7, more preferably in the range 1–4. When choosing the alkyl group attention should be paid to the surfactant character of the monomer and, if necessary, the alkyl residue has to be adjusted accordingly in order to avoid the formation of foam which can have a disruptive effect in some polymerization processes. The polyoxyalkylene glycol chain is preferably composed of ethylene oxide and/or propylene oxide, whereby the solubility of the cross-linker in the watery monomer solution can be adjusted by the ratio of EO/PO. The content of alkyl glycol units in the chain is in the range 1–45, preferably in the range 1–30, and at best In the range 5–25. The monomers according to formula 11 or their mixtures are used at up to 0.1–10% by weight, preferably at 0.5–5% by weight, or more preferably at 1.0–3.5% by weight with regard to the whole monomers. The monomers mentioned in II are commercially available, e.g. the methyl polyethylene glycol methacrylates from the firm Interorgana under the name Bisomer MPEG(x)MA (x=350, 1000, 2000).

According to this invention the cross-linking agents to be used according to formula III are esters from polyhydroxy compounds with unsaturated carboxylic acids, a preferred form of which are alkoxylated. It is preferred to use C3-6-polyhydroxy compounds with 2–4 hydroxyl groups as starting compounds for the synthesis of such cross-linkers such as trimethylol propane, glycerine, pentaerythritol, 1,3propandiol, propylene glycol or 1,4 butandiol. if before esterification alkoxylation of the alcohol occurs, it is preferable to use ethylene oxide. It is preferable to use alkoxylated polyhydroxy compounds from u=1, preferably from u=3. it is preferable to use (meth)acrylic acid as the acidic component. In a further preferred form of the cross-linking agent III polyethylene glycol di(meth)acrylate is used. In a particularly preferred form of cross-linking agent III di- or triallylamine and/or N,N-methylanebisacrylamide and/or bisacrylamido acetic acid are used. Also, mixtures of the last-mentioned cross-linking agents with the previously mentioned carboxylic acid esters of the polyhydroxy compounds exhibit an excellent activity. The cross-linkers in formula III or their mixtures are used at 0.01–1.0% by weight, preferably at 0.05–0.6% by weight, more preferably 0.05–0.3% by weight with regard to the monomers. According to this invention the cross-linkers according to III are partly available commercially, e.g. trimethylol propane oxethylate triacrylate from the firm Cray Valley under the name Sartomer SR 415 (20 EO), Craynor 435 (15 EO), Sartomer RO 208 (9 EO), Sartomer 454 (3 EO), and pentaerythritol oxethylate tetraacrylate under the name Craynor SR 494 (5 EO) and Servocure RTT 192 (5 EO) from the firm Servo Delden BV, glycerine ethoxylate triacrylate (5,5 EO) under the name Sartomer 921 and glycerine propoxylate triacrylate under the name Sartomer 9021 from the firm Cray Valley, as well as polyethylene glycol-400-diacrylate as Craynor SR 344 and polyethylene glycol600dimethacrylate as Craynor SR 252 from the firm Cray Valley.

Surprisingly it turned out that with the new cross-linker/monomer combination mutual solubilization of the cross-linker components, both soluble and insoluble in the watery monomer solution, is possible. This also makes the use of cross-linking agents possible which cannot normally be used, or only in extremely limited amounts, due to their poor solubility.

In a further favored method the use of mixtures of highly and slightly alkoxylated cross-linkers/monomers according to I, II and III in the cross-linking of the new superabsorbers has proved its worth.

The newly invented polymer for absorbing watery liquids is obtained by polymerization of ethylenically unsaturated monomers bearing acid groups, for example from acrylic acid, methacrylic acid, vinyl acetic acid, maleic acid, 2-acrylamido-2-methyl propane sulfonic acid, vinyl sulfonic acid, (methyl)allyl sulfonic acid or their mixtures in the presence of the cross-linker/monomer combination of the components I, II and III. The ratio of these acidic monomers in the monomer mixture is 55–99% by weight.

The acidic monomers are at least 25% mole, preferably 50% mole, more preferably 50 to 80% mole neutralized and are present, for example, as sodium, potassium or ammonium salt or their mixtures. Neutralization is carried out either by the addition of the corresponding alkali or ammonium hydroxides or with the corresponding carbonates or hydrogen carbonates.

Optionally, the newly invented polymers can contain further comonomers in order to modify their properties. Such comonomers can be, for example, (meth)acrylamide, (meth)acryl nitrile, vinyl pyrrolidone, vinyl acetamide, hydroxy ethyl acrylate, alkyl aminoalkyl (meth)acrylates, alkyl amino-propyl acrylamides, acryl amidopropyl trimethyl ammonium chloride or their mixtures. Such comonomers should not exceed a proportion of 40% by weight as they may negatively affect the swelling capacity of the superabsorber.

The newly invented polymers may contain water-soluble polymers as a graft basis in quantities of up to 30% by weight. These include, among others, partly or fully saponified polyvinyl alcohols, starch or starch derivatives, cellulose or cellulose derivatives, polyacrylic acids, polyglycols or their mixtures. The molecular weights of the polymers added as a graft basis have to be adapted to the polymerization conditions. It may be necessary, for example in the case of a watery solution polymerization, for reasons of the viscosity of the polymer solution, to use only low or medium molecular polymers, whereas in suspension polymerization this factor plays a minor role.

Besides polymers which are obtained by cross-linking polymerization of partly-neutralized acrylic acid, it is preferable to use those containing additional proportions of graft polymerized starch or polyvinyl alcohol.

The production of the newly invented superabsorber takes place principally according to two methods:

According to the first method the partly neutralized acrylic acid in a watery solution in the presence of the cross-linker/monomer combination of I, II and III as well as any necessary polymer additives is transformed into a gel by radical polymerization which is then reduced in size, dried, ground, re-cross-linked and sieved down to the desired particle size. The solution polymerization can be carried out continuously or discontinuously. The patent literature contains a broad spectrum of possible variations with regard to the concentration ratios, temperatures, type and quantity of the initiators as well as a multitude of re-cross-linking possibilities. Typical processes are described in the following patent specifications, which are herewith intended to become a part of the newly invented manufacturing process: U.S. Pat. No. 4,076,663, U.S. Pat. No. 4,286,082, DE 27 06 135, DE 35 03 458, DE 40 20 780, DE 42 44 548, DE 43 23 001, DE 43 33 056, DE 44 18 818.

The second method includes the inverse suspension and emulsion polymerization process. In these processes a watery, partly neutralized acrylic acid solution is dispersed with the help of protective colloids and/or emulsifiers in a hydrophobic, organic solvent and polymerization started by radical initiators. The cross-linking agents are either dissolved in the monomer solution and are dosed with this together or separately, and if necessary added subsequently. The addition of any polymer graft bases which may be present is carried out via the monomer solution or by direct addition into the oil phase. After the end of the polymerization the water is removed azeotropically from the reaction mixture and the polymer product filtered off. Surface cross-linkage of the polymer particles can be carried out in the suspension as well as subsequently on the isolated polymer powder. The principle of the procedure is described, for example, in patent specifications U.S. Pat. No. 4,340,706, DE 37 13 601, DE 28 40 010 and should be considered as part of the newly invented manufacturing process.

The addition of the subsequent cross-linking agent is often carried out to advantage in the form of a solution in water, organic solvents or their mixtures, in particular when small quantities of re-cross-linking agent are used. Suitable mixing machines for the application of the re-cross-linking agent are, for example, Patterson-Kelly mixer, DRAIS eddy mixer, Lödige mixer, Ruberg mixer, screw mixer, pan mixer and fluidized bed mixer as well as continuously working vertical mixers in which the powder is mixed at a high frequency by means of rotating knives (Schugi mixer). After the re-cross-linking agent has been mixed with the pre-cross-linked polymer heating is carried out up to temperatures of 120° to 250° C., preferably up to 135° to 200° C., more preferably up to 150° to 185° C. in order to carry out the re-cross-linking reaction. The length of the subsequent heating is limited by the point at which the desired set of properties of the superabsorber is destroyed again as a result of heat damage.

The newly invented superabsorbers show an unprecedented combination of favorable properties. Due to the positive influence of the cross-linker/comonomer combination the high retention of the polymer present before re-cross-linking is stabilized to such an extent that after the surface re-cross-linking a retention of over 30 g/g is still measured.

After the absorption of fluid, whose rate is less than 40 seconds, preferably less than 35 seconds, more preferably less than 30 seconds, the swollen gel particles stand out due to their dry handle, i.e. they do not possess the undesired wet, sticky surface which arises with Insufficient cross-linking/re-cross-linking. In addition, together with the high retention the soluble contents after 1 hour are less than 6.5%, preferably less than 5% or after 16 hours less than 10%, preferably less than 8%. The liquid absorption under a pressure (AUL) of 63 g/cm$^2$ (0.9 psi) Is greater than 20 g/g, preferably greater than 23 g/g, more preferably greater than 25 g/g.

Due to the cross-linker/monomer combination according to the present invention the superabsorbers obtain an excellent permeability for liquids in swollen condition under load. The cross-linker/monomer combination according to the present invention provides an efficient and lasting surface cross-linkage of the polymer. This makes it possible to produce superabsorbers which, after a loading test to examine the stability of surface cross-linkage (SDOV="Stabilität der Oberflächenvernetzung"), still have AUL values (63 g/cm$^2$) of at least 18 g/g, preferably of greater than 20 g/g, and most preferably of greater than 22 g/g.

The swelling pressure of the newly-invented polymers is high and after 20 minutes is at least 600 g, preferably at least 800 g, more preferably greater than 900 g.

The newly-invented hydrophilic superabsorbers are used everywhere where watery liquids have to be absorbed. This includes, for example, the generally known applications for superabsorbers in hygiene articles in the form of diapers for small children and incontinence products for adults, in ladies' napkins, in plasters, in food packagings, in the field of agriculture for plant raising, in cable insulation, in absorbent layers made of paper, water-soluble polymers and thermoplastic man-made materials and foams as well as carriers for active substances with the task of delayed release to the environment.

In the following examples the manufacture and properties of the newly-invented polymers are explained and in the chapter on testing methods the regulations governing the determination of the properties of superabsorbers are described.

Test Methods

1. Retention

The retention is measured according to the method described in EP 514 724 (page 4, lines 6–22).

2. Fluid Absorption under Pressure (AUL)

The fluid absorption under pressure (AUL) is determined according to the method described in EP 514 724 (page 4, lines 23–28). AUL 63 is measured at a pressure of 63 g/cm$^2$ (0.9 psi), AUL 21 (0.3 psi) at 21 g/cm$^2$.

3. Soluble Contants(LA)

The soluble contents (1 hour and 16 hours) are determined as described in U.S. Pat. No. 4,654,039, with the exception that a 0.9% sodium chloride solution is used as test fluid instead of synthetic urine.

4. Residual Monomers (RM)

The residual monomers (RM) are determined from the filtrate from the determination of the soluble components by means of the HPLC method, and evaluated according to the method of the internal standard.

5. Swelling Pressure (SP)

The swelling pressure is determined in a Stevens LFRA Texture Analyser (setting: speed: 1.0 mm/sec; distance 00, hold position). To this purpose 0.500 g of the powder is weighed into a measuring cylinder of 7.4 cm height and 2.7 cm diameter (grain fraction 300–600 mm), to which 10 ml of 0.9 % sodium chloride solution is added. Then the measuring cylinder (height 3.5 cm, diameter 2.5 cm) is placed into the cylinder until the distance of the level of the lower edge of the cylindrical measuring body amounts to 12 mm from the surface of the sample in the measuring cylinder. Owing to the gel expansion the measuring cylinder is pushed upwards against a two-way force-measuring cell and is indicated at the device in grams. The swelling pressure SP is measured after different periods of time.

6. Absorption against Pressure with reduced suction surface (AAP-A$_x$

This test determines a superabsorbers capability of sucking liquid out of a liquid reservoir under a defined pressure. This is carried out by means of a cylinder unit having a reduced suction surface. In contrast to the usual method of determining the Absorption against Pressure, the liquid transport in xy-direction (permeability) in the gel layer is also observed. The measuring apparatus described in EP 640 330, page 14, is used as cylinder unit for measuring. This apparatus is modified such that part of the sieve bottom is covered with a layer which is impermeable to liquids. In the middle of the sieve bottom, centrally arranged, there is left a circular aperture through which liquid absorption takes place. The remaining suction surface may amount, for example, to 9, 14, 17, 25, 34, or 60% of the original surface of 28.27 cm$^2$. The percentage suction surface, relative to the usual AAP-surface of 28.27 cm$^2$, is indicated as index Ax:

-AAP-A$_g$ (suction surface Ø 18 mm)
-AAP-A$_{14}$ (suction surface Ø 23 mm)
-AAP-A$_{17}$ (suction surface Ø 25 mm)
-AAP-A$_{25}$ (suction surface Ø 30 mm)
-AAP-A$_{34}$ (suction surface Ø 35 mm)
-AAP-A$_{60}$ (suction surface Ø 48.5 mm)

0.900±0.005 g of the superabsorber is weighed in and sprinkled as uniformly as possible onto the sieve fabric of the plastic cylinder (Ø=6 cm, height=5 cm, sieve fabric: 400 mesh=37 μm) located in the bottom, and is then loaded with a defined weight. The load optionally amounts to 20 g/cm$^2$ or 50 g/cm$^2$. The cylinder unit (Plexiglass-cylinder with sieve fabric of reduced surface, SAP, covering plate, and weight) is weighed and placed on a filter plate (Ø=12 cm, porosity=0, e.g. Schott ceramic filter Duran) which is impregnated with liquid and covered with filter paper (Schleicher und Schüll, Schwarzband 589, Ø=11 cm). The filter plate lies in the liquid up to its upper edge. In general, 0.9% NaCl-solution is used, other test solutions, such as synthetic urine, may also be used. Supernatant liquid is to be avoided. The SAP is allowed to suck for a defined period. In general, the residence time amounts to 60 minutes; optionally other periods are possible. The Absorption against Pressure with reduced suction surface (AAP-A$_x$) can be determined by re-weighing the cylinder unit. At least one double determination is to be carried out each time. In order to calculate the percentage capacity, the AAP-value with the corresponding load is also determined. Calculation of the surface-reduced AAP-A$_x$-value is effected according to the following fomula:

$$\{AAP - A_x\} = \frac{B - A}{E} \ [g/g]$$

$$\text{Capacity} = \frac{\{AAP - A_x\} \cdot 100}{AAP} \ [\%]$$

{AAP-A$_r$} : Absorption against Pressure with reduced suction surface [g/g]

A : Weight of the cylinder unit prior to sucking [g]
B : Weight of the cylinder unit after sucking [g]
E : Initial weight of superabsorber [g]

7. Stability test of surface cross-linkage (SDQV)

A cylindrical hollow body made of corundum with an internal diameter and an internal length of approximately 8 cm is filled with 20 g of superabsorber powder and approximately 130 g of cylindrical corundum particles which have a diameter and length of 1.27 cm each, and then rotated at a rate of 150 r.p.m. After 10 minutes the stability test is terminated and the absorption under pressure determined (AUL 63).

8. Rate of Liquid Absorption (SG)

In this test the time is measured in which 1 g of superabsorber absorbs 20 g of a 0.9 % sodium chloride solution at room temperature. The method of this test is described in EP 443 627, page 12, "Free Swell Rate".

EXAMPLES

Comparative Example I a) 400 kg/h of a 33% monomer solution made of acrylic acid, partly neutralized with sodium hydroxide solution at 70% mole, 3.5% by weight (relative to the acrylic acid) methoxy polyethylene glycol (22EO) methacrylate, 0.35% by weight (relative to the acrylic acid), trimethylol propane triacrylate, and 0.4% by weight sodium carbonate (relative to the acrylic acid) is rinsed continuously with nitrogen and mixed at 4–5° C. with the following catalyst solutions: 100 ppm hydrogen peroxide, 150 ppm sodium peroxide sulfate and 100 ppm azoisobutyroamidine dihydrochloride. For continuous polymerization on an endless loop 15 ppm of ascorbic acid is added. After 40 minutes polymerization time the gel produced is reduced to small pieces and dried on a belt drier at an air temperature of 160° C.

After grinding and sieving off to 150–850 μm the polymer is put into temporary storage.

Properties of the starting product:
Retention: 39.5 g/g
Soluble contents after 1 hour: 9.3%
Soluble contents after 16 hours: 14.1% b) Re-cross-linking of the starting product:

The powdery polymer obtained after comparison 1 a) is sprayed continuously at a rate of 80 kg/h in a paddle mixer (2000 r.p.m.) with 1.5% of a solution of 1 part of ethylene carbonate and 2 parts of water and warmed in a paddle drier equipped with heated mixed elements.

Steaming temperature: 190° C.
Heating area: 1.6 m$^2$
average holding time 20 min.

After the product has cooled protective sieving is carried out at 850 μm. Properties of the re-cross-linked product:
Retention: 33.5 g/g
AUL (21 g/cm$^2$): 31 g/g
AUL (63 g/cm$^2$): 18 g/g
Soluble components after 1 hour: 6.4%
Soluble components after 16 hours: 11.0%
SG: 33 s
AUL (63 g/cm$^2$)n. SDOV: 12 g/g
QD(20'): 496 g Comparative Example 2 a) As in comparison 1 a) 400 kg/h of a 33% monomer solution made of acrylic acid partly neutralized with sodium hydroxide solution at 70% role and 0.3% by weight 15 EO trimethylol propane triacrylate is continuously initiated, polymerized and worked up to a powdery resin.
Retention: 42 g/g
Soluble contents after 1 hour: 12.0 %
Soluble contents after 16 hours: 19.5% b) Re-cross-linking

The powdery polymer produced according to comparison 2a) is treated as in comparison 1b). The resulting product properties are as follows:
Retention: 31 g/g
AUL (21 g/cm$^2$): 30 g/g
AUL (63 g/cm$^2$): 17 g/g
Soluble contents after 1 hour: 6.5%
Soluble contents after 16 hours: 20.5%
SG: 62 s
AUL (63 g/cm$^2$) according to SDOV: 12 g/g
QD (20'): 528 g Example 1 a) As in comparison example 1a) a 70% mole partly neutralized acrylic acid solution which contains—relative to acrylic acid—3.5% methoxy polyethylene glycol (22EO) methacrylate, 0.2% trimethylol propane triacrylate, 0.3% polyethylene glycol (10 EO) monoallyl ether acrylate is polymerized and worked up to a powdery resin with the following properties:
Retention: 41 g/g
Soluble contents after 1 hour: 6.1%
Soluble contents after 16 hours: 9.5% b) Re-cross-linking

The powdery polymer produced according to example 1a) is after-treated as in comparison example 1b) and has the following properties:
Retention: 34 g/g
AUL(21 g/cm$^2$): 34 g/g
AUL(63 g/cm$^2$): 25.5 g/g
Soluble components after 1 hour: 4.8%
Soluble components after 16 hours: 9.4%
SG: 30 s
AUL (63 g/cm$^2$ according to SDOV: 19 g/g
QD (20'): 810 g Example 2 a) As in comparison example 1a) 400 kg/h of an acrylic acid solution partly neutralized to 70% mole which—relative to acrylic acid—contains 3.5% methoxy polyethylene glycol (22EO) methacrylate, 0.2% trimethylol propane triacrylate and 0.4% polyethylene glycol (10EO) monoallyl ether acrylate is polymerized, dried, ground and sieved off to a particle size fraction of 150–850 μm.
Retention: 38.5 g/g
Soluble components after 1 hour: 5.8%
Soluble components after 16 hours: 7.6% b) Re-cross-linking:

The polymer produced according to example 2 is coated as in comparison example 1b) and treated thermally. It has the following characteristic data:
Retention: 32 g/g
AUL (21 g/cm$^2$): 33.5 g/g
AUL (63 g/cm$^2$): 25.5 g/g Soluble contents after 1 hour: 4.8%

Soluble contents aftre 16 hours: 7.0%

SG: 33 s

AUL (63 g/cm$^2$) according to SDOV: 20 g/g

QD (20'): 960 g

Example 3 (W75067)

a) As in comparison example 1a) 400 kg/h of an acrylic acid solution partly neutralized to 70% mole containing—relative to acrylic acid—3.5% methoxy polyethylene glycol (22EO) methacrylate, 0.3% 3-EO-trimethylol propane triacrylate and 0.4% polyethylene glycol (10EO) monoallyl ether acrylate is polymerized by the addition of the initiators mentioned in comparison example 1a). The gel produced is reduced in size, dried, ground and sieved down to 150–850 μm. The following properties were found in the starting product:

Retention: 36 g/g

Soluble components after 1 hour: 5.0%

Soluble components after 16 hours: 6.6% b) Re-cross-linking

As in comparison example 1b) 80 kg/h of polymer from example 3a) is mixed with 1.5% ethylene carbonate solution and then warmed in the paddle drier. The polymer produced shows the following characteristic data:

Retention: 32 g/g

AUL (21 g/cm$^2$): 34 g/g

AUL (63 g/cm$^2$): 24 g/g

Soluble contents after 1 hour: 2.7%

Soluble contents after 16 hours: 6.8%

SG: 28 s

AUL (63 g/cm$^2$) according to SDOV: 18 g/g

In Examples 4–20 and Comparative Examples 3–8 polymerization and re-cross-linking are carried out according to the following recommended recipe:

In a cylindrical plastic vessel a polymerisation preparation of altogether 1000 g is made up. To this purpose 280 g acrylic acid as well as the cross-linking agent, comonomers and further components to be used are prepared in completely softened water. Whilst being stirred and allowed to cool this is then partly neutralized with 50% sodium hydroxide solution to a degree of neutralization of 70%. The solution is cooled down to 7°–8° C. and nitrogen bubbled through until the oxygen content of the monomer solution has dropped to a level below 0.2 ppm. Then 100 ppm of azo-bis(2-amidinopropane) dihydrochloride dissolved in 10 g VE water, 300 ppm sodium persulfate, dissolved in 6 g VE water and 70 ppm hydrogen peroxide (35%) dissolved in 1 g VE water are added. Then polymerization is started by the addition of 9 ppm ascorbic acid in 2 g water, resulting in a marked rise in temperature. After the end of the polymerization the gel-like polymer block is reduced in size, ground and dried. The polymer is then ground and sieved down to the grain fraction 150–800 μ.

Re-cross-linking: 100 g of the sieved polymer is mixed thoroughly with a solution of 0.5 g ethylene carbonate, 2 g VE water and 4 g acetone and then heated 25 min to a temperature of 180° C. in an oven.

The composition of the superabsorbers with regard to the cross-linkers, comonomers and further components as well as the properties of the product are listed in tables 1 to 3.

It can be seen from the table that the newly-invented polymers have a combination of good properties;

| | |
|---|---|
| Retention | >30 g/g |
| Absorption under pressure (49 g/cm$^2$) | >20 g/g |
| Absorption under pressure (63 g/cm$^2$) after SDOV | >18 g/g |
| Rate of liquid up-take | <40 s |
| Soluble contents (16 h) | <10% |
| Swelling pressure (20 min) | >800 g |

In the comparative examples it can be seen that by varying the amount of cross-linker it is possible to attain individual measured values but not the entire combination of the good properties.

Example 21–24

As in Example 1 further experiments were carried out with the following cross-linker/monomer combinations, the quantities relate to %-wt. acrylic acid:

| | Example 21 (Code W 75068) | Example 22 (Code W 75069) | Example 23* (Code W 76164) | Example 24 (Code W 76165) |
|---|---|---|---|---|
| Cross-linker/Comonomer | | | | |
| TMPTA-15EO | 0.4 | | | |
| TMPTA-3EO | | | | 0.3 |
| PE-5EO-TA | | | 0.14 | |
| AA-10EO-A | 0.2 | 0.2 | 0.4 | 0.4 |
| TMPTA | | 0.2 | | |
| MPEG1000MA | 3.5 | 3.5 | 2.9 | 1.67 |
| Product properties (re-cross-linked) | | | | |
| Retention [g/g] | 32.5 | 33.5 | 34 | 29.5 |
| AUL 63 [g/g] | 25.5 | 25 | 23.5 | 25 |
| AUL 63 acc. SDOV [g/g] | 20 | 20 | 18 | 22 |
| AAP 50 A$_{34}$ [g/g] | | 16.5 | 17 | 23.5 |
| AAP 50 A$_{34}$ [%] | | 63 | 65 | 92 |
| LA 1 h [%] | 3.0 | 3.5 | 2.2 | 2.5 |
| LA 16 h [%] | 8.2 | 9.3 | 6.4 | 5.5 |

*: Example 24 was carried out without the addition of sodium carbonate

Example 25–30

According to the general formulation of Examples 4–20 further superabsorbent polymers according to the present invention were produced using triallylamine as cross-linker component III. In Example 27, 0.4 g sodium carbonate were added after neutralization of the acrylic acid. The results are shown In Table 4.

Example 31

According to the general formulation of Example 1 a test was carried out with a cross-linker/monomer combination of 2.5%-wt. methoxypolyethylene glycol(22EO)-methacrylate, 0.35%-wt. polyethylene glycol(10EO)-monoallyl etheracrylate, and 0.12%-wt. triallylamine. The starting product had a retention of 38 g/g, the re-cross-linked product had a retention of 32.5 g/g, an AUL (63 g/cm$^2$) of 26.5 g/g, an AUL according to SDOV of 20 g/g, a swelling pressure of 1340 g (after 20'), and 1080 g (after 2h), and 6.4% soluble contents (after 16h).

Comparative Example 9 and Examples 32–34

These examples show the improved permeability in the swollen gel layer by using methoxypolyethylene glycol methacrylate as comonomer. The results are summarized in Table 5.

Example 32

According to the general formulation of Example 1 a test was carried out using a cross-linker/monomer combination of 1%-wt. methoxypolyethylene glycol(17EO)methacrylate, 0.3%-wt. polyethylene glycol(10EO)monoallyl ether acrylate, and 0.1%-wt. 3-EO-trimethylolpropane triacrylate. The starting product had a retention of 37.5 g/g, the re-cross-linked product had a retention of 32.5 g/g, an AUL (63 g/cm$^2$) of 23.5 g/g, and 8.5% soluble contents (after 16h).

Example 33

According to the general formulation of Example 1 a test was carried out using a cross-linker/monomer combination of 2%-wt. methoxypolyethylene glycol( 17EO)-methacrylate, 0.3%-wt. polyethylene glycol (10EO)-monoallyl ether acrylate, and 0.1%-wt. 3-EO-trimethylolpropane triacrylate. The starting product had a retention of 37.5 g/g, the re-cross-linked product had a retention of 31.5 g/g, an AUL (63 g/cm$^2$) of 24.5 g/g, and 8.5% soluble contents (after 16h).

Example 34

According to the general formulation of Example 1 a test was carried out using a cross-linker/monomer combination of 3%-wt. methoxypolyethylene glycol(17EO)-methacylate, 0.3%-wt. polyethylene glycol(10EO)-monoallyl ether acrylate, and 0.1%-wt. 3-EO-trimethylolpropane triacrylate. The starting product had a retention of 39 g/g, the re-cross-linked product had a retention of 32 g/g, an AUL (63 g/cm$^2$) of 23.5 g/g and 6.5% soluble contents (after 16h).

Comparative Example 9

According to the general formulation of Example 1 a test was carried out using a cross-linker/monomer combination without methoxypolyethylene glycol(17EO)-methacrylate and consisting of 0.3%-wt. polyethylene glycol(10EO)-monoallyl ether acrylate and 0.1%-wt. 3-EO-trimethylolpropane triacrylate. The starting product had a retention of 33 g/g, the re-cross-linked product had a retention of 32 g/g, an AUL (63 g/cm$^2$) of 19.5 g/g and 7.6% soluble contents (after 16h).

Comparative Examples 10–12

The AAP50-$A_{34}$ value is determined in commercially available superabsorbers. The measured values prove that the products do not reach the limiting values demanded according to the present invention (Table 6).

TABLE 1

| Example | Cross-linker III TMPTA-3EO [% by weight] | Cross-linker I AA-10EO-MA AA-10EO-A [% by weight] | Monomer II MPEG1000MA [% by weight] | Starting Product Retention [g.g] | Re-cross-linked Product Retention [g.g] | AUL 63 [g.g] | AUL63 acc. SDOV | AAP 50 $A_{34}$ [g/g] | AAP 50 $A_{34}$ [%] | RM acr. acid [ppm] | L.A. 1 h [%] | L.A. 16 h [%] |
|---|---|---|---|---|---|---|---|---|---|---|---|---|
| 4 | 0.2 | 0 | 3 | 38.4 | 30.2 | 25.5 | 20.5 | | | 960 | | 8.8 |
| 5 | 0.1 | 0.2 A | 3 | 40.6 | 31.2 | 26.5 | 23 | | | 510 | 3.8 | 9.2 |
| 6 | 0.15 | 0.25 A | 3 | 37.1 | 30.5 | 25 | 24 | 22.5 | 94 | 640 | 3.1 | 7.1 |
| comp. 3 | 0.15 | 0.25 A | 0 | 32.3 | 28.6 | 25.5 | 22 | | | 1610 | | 7.7 |
| 7 | 0.15 | 0.25 MA | 3 | 38.1 | 30.6 | 25.5 | 24 | | | 940 | | 8.8 |
| comp. 4 | 0.15 | 0.25 | 3 (MAC 13/20) | 40 | 34 | 22.5 | 15 | | | 800 | | 13 |
| comp. 5 | 0.15 | 0.25 A | 1.5 (MAC 13/20) | 38.8 | 31.8 | 25.5 | 17.5 | | | 1050 | | 12 |

TMPTA-3EO: Triacrylate of a trimethylopropane ethoxylated with 3 mole EO
AA-10EO-MA: Methacrylate ester of an allyl alcohol ethoxylated with 10 mole EO
AA-10EO-A: Acrylate ester of an allyl alcohol ethoxylated with 10 mole EO
MPEG 1000 MA: Methoxy polyethylene glycol (22 mole EO) methacrylate
MAC 13/20: C13-polyethylene glycol (20 mole EO) methacrylate

TABLE 2

| Example | Cross-linker III PE-5EO-TA [% by weight] | Cross-linker I AA-10EO-MA AA-10EO-A [% by weight] | Monomer II MPEG1000MA [% by weight] | Starting Product Retention [g/g] | Re-cross-linked Product Retention [g/g] | AUL 63 [g/g] | AUL63 acc. SDOV [g/g] | RM acrylic acid [ppm] | L.A. 16 h [%] |
|---|---|---|---|---|---|---|---|---|---|
| 8 | 0.15 | 0.25 A | 3 | 38.7 | 31.5 | 24.5 | 19 | 605 | 9 |
| 9 | 0.1 | 0.35 A | 3 | 36.2 | 32 | 23.5 | 20.5 | 660 | 8 |
| 10 | 0.15 | 0.25 MA | 3 | 37.2 | 31 | 24 | 19.5 | | 8.5 |
| 11 | 0.15 | 0.3 MA | 3 | 36.8 | 31 | 25 | 20 | | 7.7 |
| 12* | 0.1 | 0.35 A | 2 | 37.4 | 30.2 | 24 | 19 | 800 | 8.3 |
| 13* | 0.1 | 0.35 MA | 2 | 36.2 | 30.9 | 24 | 18.5 | 800 | 8.4 |
| comp.6 | 0.1 | 0.35 A | 0 | 32.7 | 30.5 | 21 | 16.5 | 650 | 6.5 |
| 14 | 0.1 | 0.3 A | 3 | 38.5 | 31 | 24.5 | 20.5 | 740 | 8.9 |

TABLE 2-continued

| Example | Cross-linker III PE-5EO-TA [% by weight] | Cross-linker I AA-10EO-MA AA-10EO-A [% by weight] | Monomer II MPEG1000MA [% by weight] | Starting Product Retention [g/g] | Re-cross-linked Product | | | | |
|---|---|---|---|---|---|---|---|---|---|
| | | | | | Retention [g/g] | AUL 63 [g/g] | AUL63 acc. SDOV [g/g] | RM acrylic acid [ppm] | L.A. 16 h [%] |
| comp.7 | 0.1 | +0.05 MAPEG-MA 0.3 A +0.05 MAPEG-MA | 0 | 31.7 | 30 | 22.5 | 16.5 | 970 | 6.9 |
| 15 | 0.1 | 0.25 MAPEG-MA | 3 | 35 | 32.2 | 24.5 | 18 | 1200 | 9 |

PE-5EO-TA: pentaerythrite-pentaethoxylate-tetraacrylate
PVA: polyvinyl alcohol
MAPEG-MA: methacrylic polyethylene glycol (15EO) methacrylate
*Example 12 and 13 are prepared with PVA (0.5% by weight) Mowiol 5/88

TABLE 3

| Exam. | Cr.-linker III TMPTA-15EO | Monomer II MPEG1000MA [% by weight] | Starting Product Retention [g/g] | Re-cross-linked Product | | | | | | | | | | |
|---|---|---|---|---|---|---|---|---|---|---|---|---|---|---|
| | | | | Retention [g/g] | AUL 63 [g/g] | AUL63 acc. to SDOV [g/g] | AAP50 $A_{34}$ [g/g] | AAP50 $A_{34}$ [%] | Swelling Pressure | | | | RM acrylic acid [ppm] | LA | |
| | | | | | | | | | 20' | 2h | 4h | 16h | | 1 h [%] | 16 h [%] |
| comp. 8 | 0.25 | 0 | 36.6 | 30.5 | 26.5 | 16.5 | | | 1225 | 975 | 850 | 590 | 1100 | 4 | 10 |
| 16 | 0.25 | 1.5 | 38.2 | 31 | 26.5 | 21 | 23.5 | 89 | 1125 | 925 | 812 | 575 | 960 | 4.5 | 9 |
| 17 | 0.25 | 3 | 40.1 | 31.2 | 26 | 22.5 | | | 1095 | 865 | | | 770 | 4.5 | 9 |
| 18 | 0.25 | 5 | 40.3 | 31.2 | 25.5 | 24 | 21.5 | 98 | 1095 | 713 | | | 590 | 5 | 9.5 |
| 19 | 0.25 | 3(MPEG 350 MA) | 38 | 31.2 | 25 | 22 | | | | | | | 755 | 3.6 | 8.6 |
| 20 | 0.25 | 3(MPEG 2000 MA) | 37.6 | 32.2 | 25 | 22 | | | | | | | 805 | 4.5 | 9.4 |

TMPTA-15EO: Triacrylate of a trimethylol propane ethoxylated with 15 mole EO
MPEG 350 MA: Methacrylate ester of a methoxy polyethylene glycol with 8 mole EO
MPEG 2000 MA: Methacrylate ester of a methoxy polyethylene glycol with 45 mole EO

TABLE 4

| Examp. | Cross-linker I + III TAA/ AA-10EO-A/ | Monomer II MPEG 1000 MA [%-wt.] | Starting product Retention [g/g] | Re-cross-linked product | | | | | | | | | |
|---|---|---|---|---|---|---|---|---|---|---|---|---|---|
| | | | | Retention [g/g] | AUL 63 [g/g] | AUL 63 acc. SDOV [g/g] | Swelling pressure [g] | | | | RM acryl. ac. [ppm] | LA 1 h [%] | 16 h [%] |
| | | | | | | | | 20' | 2h | 4h | 16h | | | |
| 25 | 0.1/0.2/0 | 2 | 38.5 | 32 | 27 | 24 | 1300 | 1060 | | | 400 | | 7.2 |
| 26 | 0.1/0.3/0 | 2 | 38 | 31.5 | 26.5 | 23.5 | | | | | 430 | | 5.8 |
| 27 | 0.1/0.3/0 | 2 | 37.5 | 32 | 27 | 23 | | | | | | | |
| 28 | 0.1/0.4/0 | 2 | 36.5 | 31 | 26.5 | 22 | | | | | 450 | | 5.9 |
| 29 | 0.1/0.1/ 0.1 (PEG600DA) | 2 | 38.5 | 33 | 27 | 21 | | | | | 520 | | 6.0 |
| 30 | 0.1/0.15/ 0.05(TMPTA) | 2 | 36.5 | 31.5 | 26 | | | | | | 800 | | 5.5 |

TMPTA: Trimethylolpropane triacrylate
TAA: Triallylamine
PEG600DA: Diacrylate ester of a polyethylene glycol of molecular weight 600
AA-10EO-A: Acrylate ester of an allyl alcohol ethoxylated with 10 Mol EO
MPEG 1000 MA: Methacrylate ester of a methoxypolyethylene glycol with 22 Mol EO

TABLE 5

| Example | Cross-linker III TMPTA-3EO [%-wt.] | Cr.linker I AA-10EO-A [%-wt.] | Monomer II MPEG750 MA [%-wt.] | Start. Prod. Retention [g/g] | Re-cross-linked product Retention [g/g] | AUL 21 [g/g] | AUL 63 [g/g] | AAP 50 $A_{34}$ [g/g] | AAP50 $A_{34}$ [%] | L.A. 16 h [%] |
|---|---|---|---|---|---|---|---|---|---|---|
| Comp. 9 | 0.1 | 0.3 | 0 | 33 | 32 | 31.5 | 19.5 | 10.5 | 48 | 7.6 |
| 32 | 0.1 | 0.3 | 1 | 37.5 | 32.5 | 32 | 23.5 | 19.5 | 76 | 8.5 |
| 33 | 0.1 | 0.3 | 2 | 37.5 | 31.5 | 32 | 24.5 | 20 | 80 | 8.5 |
| 34 | 0.1 | 0.3 | 3 | 39 | 32 | 32 | 23.5 | 21 | 84 | 6.4 |

TMPTA-3EO: Triacrylate of a trimethylolpropane ethyoxylated with 3 Mol EO
AA-10EO-A: Acrylate ester of an allyl alcohol ethoxylated with 10 Mol EO
MPEG750 MA: Methoxypolyethylene glycol (17 Mol EO) methacrylate

TABLE 6

| Example | Commercial Product | AAP50-$A_{34}$ [g/g] | AAP50-$A_{34}$ [%] |
|---|---|---|---|
| Comp. 10 | Salsorb CL20 | 8.5 | 63 |
| Comp. 11 | ASAP 2000 | 14 | 74 |
| Comp. 12 | Sanwet IM 7000 | 6.5 | 43 |

We claim:

1. A cross-linked polymer useful for absorbing watery liquids, built-up of partially neutralized monomers having monoethylenically unsaturated acid groups and optionally further monomers copolymerizable therewith, wherein the polymer is manufactured with use of a combination of components $CH_2=CR^6-Co-(OCHR^3-CHR^3)_zO-CH_2-CR^6{}'CH_2$, $CH_2=CR^6-R^5-(OCHR^3-CHR^3)_vOR^4$, and

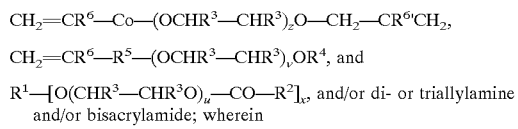, and/or di- or triallylamine and/or bisacrylamide; wherein $R^1$ is a multivalent $C_{2-10}$-alkyl,
$R^2$ is a linear or branched $C_{2-10}$-alkenyl,
$R^3$ is H, $CH_3$, or $C_2H_5$,
$R^4$ is H, or linear or branched $C_{1-10}$-alkyl,
$R^5$ is CO or $CH_2$,
$R^6$ is H or $CH_3$,
x is 2–6,
u is 0–15,
v is 1–45, and
z is 3–20,
wherein the polymer contains 0.05–1.0% by weight of component I, 0.1–10% by weight of component II, and 0.01–1.0% by weight of component III, relative to the total weight of monomers in the polymer.

2. A polymer as claimed in claim 1, which has a retention value >30 g/g, an absorption value under pressure of 49 g/cm² of >20 g/g, an absorption value under pressure of 63 g/cm² after milling of >18 g/g, a rate of absorption liquid of <40 s, a swelling pressure of >800 g, and a soluble contents of <10%.

3. A polymer as claimed in claim 1, wherein the polymer contains 0.05–0.6% by weight of component I, 0.5–5% by weight of component II, and 0.05 to 0.6% by weight of component III, relative to the total weight of monomers in the polymer.

4. A polymer as claimed in claim 1, wherein the polymer contains 0.1–0.4% by weight of component I, 1.0–3.5% by weight of component II, and 0.05–0.3% by weight of component III, relative to the total weight of monomers in the polymer.

5. A polymer as claimed in claim 1, wherein component I comprises an allyl polyethylene glycol-(meth) acrylic acid esters, component II comprises a methyl polyethylene glycol-(meth)acrylates, and component III is selected from the group consisting of trimethylolpropane oxethylate-(meth)acrylic acid esters, glycerol oxethylate-(meth)acrylic acid esters, pentaerythritol oxethylate-(meth)acrylic acid esters, polyethylene glycol-α,ω-di(meth)acrylic acid esters and di- or triallylamine, N,N-methylenebisacrylamide, and bisacrylamido acetic acid.

6. A polymer as claimed in claim 1, wherein the monomers having monoethylenically unsaturated acid groups are selected from the group consisting of acrylic acid, methacrylic acid, vinyl acetic acid, vinyl sulfonic acid, methallyl sulfonic acid, and 2-acrylamido-2-methyl propane sulfonic acid.

7. A polymer as claimed in claim 1, that comprises 0 to 40% by weight of further comonomers selected from the group consisting of (meth)acrylamide, (meth)acrylonitrile, vinyl pyrrolidone, hydroxy ethyl acrylate, and vinyl acetamide.

8. A polymer as claimed in claim 1, which comprises up to 30% by weight of water-soluble polymers as a graft basis.

9. A polymer as claimed in claim 1, which comprises a polysaccharide or polyvinyl alcohol as a graft basis.

10. A polymer as claimed in claim 1, which has been crosslinked on the surface with a re-cross-linking agent and wherein this re-cross-linkage has optionally been repeated.

11. A polymer according to claim 10, wherein the re-cross-linking agent is selected from the group consisting of polyols, polyepoxides, polyamines, and alkylene carbonates.

12. A polymer as claimed in claim 10, which has a retention of at least 30 g/g, a liquid up-take pressure at 49 g/cm² of at least 20 g/g, and a liquid up-take under pressure at 63 g/cm² after SDOV of at least 18 g/g, and a content of soluble components after 1 hour at a maximum of 6.5% and after 18 hours at a maximum of 10%, and an absorption against a pressure of 50 g/cm² with a suction surface reduced by 34% (AAP-$A_{34}$) of at least 15 g/g, and at least 50% of the initial value of the absorption against pressure without surface reduction.

13. A polymer as claimed in claim 10, which has a liquid take-up under pressure of 63 g/cm² after SDOV of at least 20 g/g, and an AAP-$A_{34}$ of at least 10 g/g.

14. A polymer as claimed in claim 10, which has a swelling pressure after 20 minutes of at least 600 g.

15. A polymer as claimed in claim 10, which has a content of soluble components after 16 hours at a maximum of 8%.

16. A polymer as claimed in claim 10, which has a liquid take-up under pressure of 63 g/cm² of greater than 23 g/g.

17. A polymer according to claim 10, which has a rate of liquid take-up of less than 40 seconds.

18. A process of making a polymer according to claim 1, which comprises polymerizing to a hydrogel (i) a watery solution of the monomers having monoethylenically unsaturated acid groups and (ii) components I, II, and III, in the presence of a radical forming agents, by solution or suspension polymerization, and crushing, drying, grounding, and sieving the hydrogel.

19. A process as claimed in claim 18, further comprising treating the polymer with a surface cross-linking agent, and wherein surface cross-linkage is carried out at an elevated temperature.

20. A process as claimed in claim 19, wherein the polymer is treated with the surface cross-linking agent several times and the surface cross-linkage is carried out several times.

21. A method of using a polymer as claimed in claim 1, comprising absorbing water or a watery liquid with the polymer.

22. A method of using a polymer as claimed in claim 1, comprising absorbing body fluids with the polymer.

23. A polymer as claimed in claim 1, comprising 55–99% by weight of the monomers having monoethylinically unsaturated acid groups, that are optionally neutralized, based on the total weight of monomers.

* * * * *